(12) United States Patent
Dickhans

(10) Patent No.: US 11,058,486 B2
(45) Date of Patent: Jul. 13, 2021

(54) SYSTEMS AND METHODS FOR PERCUTANEOUS MICROWAVE ABLATION

(71) Applicant: COVIDIEN LP, Mansfield, MA (US)

(72) Inventor: William J. Dickhans, Longmont, CO (US)

(73) Assignee: COVIDIEN LP, Mansfield, MA (US)

(*) Notice: Subject to any disclaimer, the term of this patent is extended or adjusted under 35 U.S.C. 154(b) by 1139 days.

(21) Appl. No.: 15/425,762

(22) Filed: Feb. 6, 2017

(65) Prior Publication Data
US 2017/0231695 A1  Aug. 17, 2017

Related U.S. Application Data

(60) Provisional application No. 62/293,965, filed on Feb. 11, 2016.

(51) Int. Cl.
*A61B 18/18* (2006.01)
*A61B 34/20* (2016.01)
(Continued)

(52) U.S. Cl.
CPC ...... *A61B 18/1815* (2013.01); *A61B 17/3478* (2013.01); *A61B 34/20* (2016.02);
(Continued)

(58) Field of Classification Search
CPC ............ A61B 17/3478; A61B 18/1815; A61B 2017/00955; A61B 2018/00023; A61B 2018/00577; A61B 2018/1823; A61B 2018/183; A61B 2018/1892; A61B 2034/2051; A61B 2034/254; A61B 2034/258; A61B 2090/374; A61B 2090/376; A61B 2090/378; A61B 2090/3925; A61B 2218/002; A61B 34/20; A61B 34/25; A61M 25/0102; A61M 25/0662

See application file for complete search history.

(56) References Cited

U.S. PATENT DOCUMENTS 5,720,718 A  2/1998  Rosen et al.
5,772,628 A  6/1998  Bacich et al.
(Continued)

FOREIGN PATENT DOCUMENTS

| CN | 104519950 A | 4/2015 |
|----|-------------|--------|
| WO | 2014071161 A1 | 5/2014 |
| WO | 2016/033066 A1 | 3/2016 |

OTHER PUBLICATIONS

International Search Report and Written Opinion of the International Searching Authority issued in corresponding Application No. PCT/US2017/016855, dated May 22, 2017, 17 pages.
(Continued)

*Primary Examiner* — Michael F Peffley
*Assistant Examiner* — Khadijeh A Vahdat

(57) ABSTRACT

Provided in accordance with aspects of the present disclosure is a microwave ablation system including an introducer having a lumen therethrough, a stylus configured for slidable engagement within the lumen of the introducer, and a microwave ablation antenna configured to deliver energy to a target during an ablation procedure, wherein the microwave ablation antenna is configured for slidable engagement within the lumen of the introducer.

12 Claims, 8 Drawing Sheets

(51) Int. Cl.
  *A61B 34/00* (2016.01)
  *A61B 17/34* (2006.01)
  *A61B 90/00* (2016.01)
  *A61B 17/00* (2006.01)
  *A61B 18/00* (2006.01)
  *A61M 25/01* (2006.01)
  *A61M 25/06* (2006.01)

(52) U.S. Cl.
  CPC .... *A61B 34/25* (2016.02); *A61B 2017/00955* (2013.01); *A61B 2018/00023* (2013.01); *A61B 2018/00577* (2013.01); *A61B 2018/183* (2013.01); *A61B 2018/1823* (2013.01); *A61B 2018/1892* (2013.01); *A61B 2034/2051* (2016.02); *A61B 2034/2065* (2016.02); *A61B 2034/254* (2016.02); *A61B 2034/258* (2016.02); *A61B 2090/374* (2016.02); *A61B 2090/376* (2016.02); *A61B 2090/378* (2016.02); *A61B 2090/3925* (2016.02); *A61B 2218/002* (2013.01); *A61M 25/0102* (2013.01); *A61M 25/0662* (2013.01)

(56) References Cited

U.S. PATENT DOCUMENTS

| | | | |
|---|---|---|---|
| 5,902,289 | A | 5/1999 | Swartz et al. |
| 6,090,084 | A | 7/2000 | Hassett et al. |
| 6,506,189 | B1 | 1/2003 | Rittman, III et al. |
| 6,575,969 | B1 | 6/2003 | Rittman, III et al. |
| 7,197,363 | B2 | 3/2007 | Prakash et al. |
| 7,201,731 | B1 | 4/2007 | Lundquist et al. |
| 7,301,131 | B2 | 11/2007 | Gauthier et al. |
| 7,306,595 | B2 | 12/2007 | Ostrovsky et al. |
| 7,311,703 | B2 | 12/2007 | Turovskiy et al. |
| 7,678,109 | B2 | 3/2010 | Podmore et al. |
| 8,476,242 | B2 | 7/2013 | Mon |
| 9,119,650 | B2 | 9/2015 | Brannan et al. |
| 9,247,992 | B2 | 2/2016 | Ladtkow et al. |
| 2006/0241564 | A1 | 10/2006 | Corcoran et al. |
| 2007/0077230 | A1 | 4/2007 | Mon |
| 2007/0123815 | A1 | 5/2007 | Mark |
| 2008/0097347 | A1 | 4/2008 | Arvanaghi |
| 2010/0321257 | A1* | 12/2010 | Brannan ............... H01Q 1/248 343/703 |
| 2011/0004205 | A1 | 1/2011 | Chu et al. |
| 2011/0152855 | A1 | 6/2011 | Mayse et al. |
| 2013/0006232 | A1* | 1/2013 | Pellegrino ............. A61B 18/12 606/33 |
| 2013/0165915 | A1* | 6/2013 | Thiel ..................... A61B 18/14 606/33 |
| 2013/0226172 | A1 | 8/2013 | Peterson et al. |
| 2013/0274673 | A1 | 10/2013 | Fischell et al. |
| 2015/0297246 | A1 | 10/2015 | Patel et al. |
| 2015/0366615 | A1 | 12/2015 | Brannan et al. |
| 2016/0058507 | A1 | 3/2016 | Dickhans |
| 2016/0317224 | A1 | 11/2016 | Girotto et al. |

OTHER PUBLICATIONS

Extended European Search Report issued in corresponding Appl. No. EP 17750638.3 dated Sep. 11, 2019 (7 pages).

Canadian Office Action issued in corresponding Appl. No. 3,014,352 dated Mar. 11, 2019 (6 pages).

Canadian Office Action issued in corresponding Appl. No. CA 3,014,352 dated Feb. 17, 2020 (4 pages).

Office Action issued in corresponding Chinese Appl. No. CN201780018409.8 dated Jun. 18, 2020 (10 pages) together with English language translation (11 pages).

Japanese Office Action issued in corresponding Appl. No. JP 2018-542131 dated Jan. 20, 2021 (7 pages), together with English language translation (8 pages).

* cited by examiner

SYSTEMS AND METHODS FOR PERCUTANEOUS MICROWAVE ABLATION

CROSS REFERENCE TO RELATED APPLICATIONS

The present application claims the benefit of and priority to U.S. Provisional Application Ser. No. 62/293,965, filed on Feb. 11, 2016, the entire contents of which are incorporated herein by reference.

BACKGROUND

1. Technical Field

The present disclosure relates to microwave ablation and, more particularly, to systems and methods for percutaneous microwave ablation.

2. Discussion of Related Art

Treatment of certain diseases requires the destruction of malignant tissue growths, e.g., tumors. Electromagnetic ("EM") radiation can be used to heat and destroy tumor cells. Microwave ablation for treatment of tumors is often preferred over other treatments because it is minimally invasive and achievable through small incisions made into the skin (e.g., percutaneous, laparoscopic, etc.). Treatment may involve inserting ablation antennas into or adjacent to tissues where cancerous tumors have been identified. Once the antennas are positioned, electromagnetic energy is passed through the antenna into surrounding tissue to treat, e.g., heat, ablate and/or coagulate tissue.

Often, tumors are located subcutaneously and/or surrounded by critical tissue structures, making navigation of the ablation antenna to the tumor site difficult or impossible. In such situations, addressing the tumor often requires open surgery or other invasive procedures.

SUMMARY

Provided in accordance with aspects of the present disclosure is a microwave ablation system including an introducer having a lumen therethrough, a stylus configured for slidable engagement within the lumen of the introducer, and a microwave ablation antenna configured to deliver energy to a target during an ablation procedure, wherein the microwave ablation antenna is configured for slidable engagement within the lumen of the introducer.

In an aspect of the present disclosure, an electromagnetic navigation system is provided to facilitate navigation of at least the introducer, the stylus, and the microwave ablation antenna to the target.

In another aspect of the present disclosure, the introducer is formed from a non-conductive material that allows the microwave ablation antenna to radiate microwave energy throughout an entire length of the introducer.

In yet another aspect of the present disclosure, the introducer is formed from a material selected from the group consisting of Polyether ether ketone and fiberglass.

In still another aspect of the present disclosure, the introducer has a first end, a second end, and a shaft disposed therebetween, wherein the first end has a first aperture and a fitting configured for engagement with the microwave ablation antenna and the stylus, the second end has a second aperture, and the shaft has a length, an outside diameter, and an inside diameter defined by a lumen.

In still yet another aspect of the present disclosure, the stylus is configured to articulate and adopt at least one curved configuration to navigate to the target.

In another aspect of the present disclosure, the introducer is formed from a shape-memory material and configured to adopt and maintain the at least one curved configuration of the stylus.

In yet another aspect of the present disclosure, the introducer maintains the at least one curved configuration defined by the stylus after the stylus has been removed from the introducer.

In still another aspect of the present disclosure, a fluid can be introduced into the lumen of the introducer.

In still yet another aspect of the present disclosure, the fluid is disposed between an outer surface of the microwave ablation antenna and the lumen of the introducer.

In another aspect of the present disclosure, therapeutic agents can be introduced into the lumen of the introducer.

In yet another aspect of the present disclosure, the therapeutic agents are thermo-sensitive and configured to react with the energy radiated from the microwave ablation antenna.

In still yet another aspect of the present disclosure, the electromagnetic navigation system is used in conjunction with real time ultrasound, fluoroscopy, CT, or MRI imaging.

Provided in accordance with another aspect of the present disclosure is a method of performing a microwave ablation procedure, including inserting a combination introducer and stylus into a patient at a desired location, navigating the combination introducer and stylus to a target, inserting the combination introducer and stylus into the target, removing the stylus from the introducer while leaving the introducer in the target, inserting a microwave ablation antenna into a lumen of the introducer, advancing the microwave ablation antenna through the lumen of the introducer until a radiating (portion or section of) the microwave ablation antenna is proximate the target, and radiating energy from the microwave ablation antenna through at least a portion of the introducer into the target.

In another aspect of the present disclosure, a first introducer is placed at a first target site, and a second introducer is placed at a second target site.

In yet another aspect of the present disclosure, an electromagnetic navigation system is provided to facilitate navigation of the introducer, the stylus, and the microwave ablation antenna to the targets.

In still another aspect of the present disclosure, the introducer is formed from a non-conductive material that allows the microwave ablation antenna to radiate microwave energy throughout an entire length of the introducer.

In still yet another aspect of the present disclosure, fluid is introduced into the lumen of the introducer between an outer surface of the microwave ablation antenna and an inner surface of the lumen of the introducer.

Provided in accordance with another aspect of present disclosure is at least one introducer having a lumen therethrough, a stylus configured for slidable engagement within the lumen of the at least one introducer, and a microwave ablation antenna configured to deliver energy to a target during an ablation procedure, wherein the microwave ablation antenna is configured for slidable engagement within the lumen of the at least one introducer.

In another aspect of the present disclosure, the at least one introducer is formed from a non-conductive material that allows the microwave ablation antenna to radiate microwave energy throughout an entire length of the at least one introducer.

BRIEF DESCRIPTION OF THE DRAWINGS

Objects and features of the present disclosure will become apparent to those of ordinary skill in the art when descriptions of various embodiments thereof are read with reference to the accompanying drawings, of which:

FIG. 7A is a partial exploded cross-sectional view of the schematic diagram of FIG. 7.

DETAILED DESCRIPTION OF THE DRAWINGS

The present disclosure is directed to a flexible microwave ablation antenna in combination with a stylus and an introducer. This combination can be useful in treating tumors that have limited accessibility. Specifically, the stylus, introducer, and flexible microwave ablation antenna may be customized to reach any depth and/or traverse any path within a patient's body to gain access to a tumor. The microwave ablation antenna may radiate energy through the introducer, further enhancing the versatility of the described device. These and other aspects and features of the present disclosure are detailed herein below.

Figure 1:
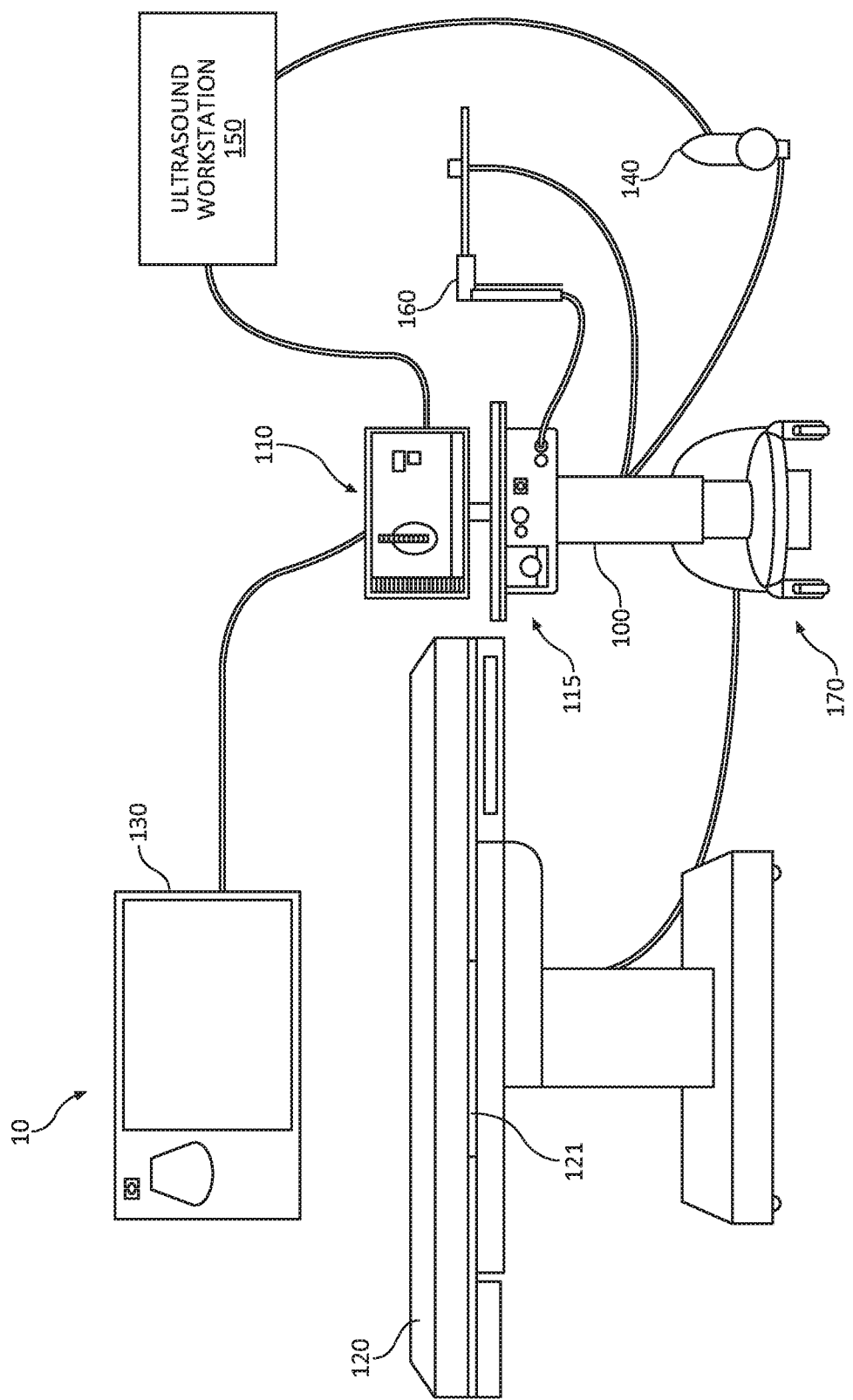
FIG. 1 is a side view of a fluid cooled microwave ablation system provided in accordance with the present disclosure.

Referring now to FIG. 1, an exemplary microwave ablation system 10 of the present disclosure is depicted. The microwave ablation system 10 includes a computing device 100 storing one or more ablation planning and electromagnetic tracking applications, a touch display computer 110, microwave ablation generator 115, an operating table 120, including an electromagnetic (EM) field generator 121, a second display 130, an ultrasound imaging sensor 140, an ultrasound workstation 150, a microwave ablation antenna assembly 160, and a base unit 170 configured to support computing device 100, the microwave ablation generator 115, and the touch display computer 110. Computing devices described herein may be, for example, a laptop computer, desktop computer, tablet computer, or other similar device. Touch display computer 110 is configured to control microwave generator 115, pump 117, microwave ablation antenna assembly 160, and other accessories and peripheral devices relating to, or forming part of, microwave ablation system 10. Touch display computer 110 is configured to present a user interface enabling a clinician to input instructions and setting for the microwave ablation generator 115, display images, and/or messages relating to the performance of the microwave ablation generator 115, the progress of a procedure, and issue alarms or alerts related to the same.

Operating table 120 may be any table suitable for use during a surgical procedure, which in certain embodiments includes or is associated with an EM field generator 121. EM field generator 121 is used to generate an EM field during the microwave ablation procedure and forms part of an EM tracking system, which is used to track the positions of surgical instruments, e.g., microwave ablation antenna assembly 160 and ultrasound sensor 140, within the EM field around and within the body of a patient. Second display 130 (FIG. 1), in association with computing device 100, may be used for displaying ultrasound imaging and providing visualization of tissue to be treated as well as navigation of the fluid cooled microwave ablation antenna assembly 160. However, it is envisioned that touch display computer 110 and computing device 100 may also be used for ultrasound imaging and navigation purposes in addition to its microwave ablation generator 115 control functions discussed above.

As will be described in more detail below (FIG. 2 and FIG. 3) microwave ablation antenna assembly 160 is used to ablate tissue, e.g., a lesion or tumor (hereinafter referred to as a "target"), by using microwave energy to heat tissue in order to denature or kill cancerous cells. Further, although an exemplary microwave ablation antenna assembly 160 is detailed herein, it is contemplated that other suitable microwave ablation antennas may be utilized in accordance with the present disclosure. For example, the ablation antennas and systems described in U.S. patent application Ser. No. 14/828,682 entitled MICROWAVE ABLATION SYSTEM, filed on Aug. 18, 2015 by Dickhans, International Application No. PCT/US15/46729 entitled MICROWAVE ABLATION SYSTEM, filed on Aug. 25, 2015 by Dickhans, U.S. patent application Ser. No. 13/836,203 entitled MICROWAVE ABLATION CATHETER AND METHOD OF UTILIZING THE SAME, filed on Mar. 15, 2013 by Ladtkow et al., U.S. patent application Ser. No. 13/834,581 entitled MICROWAVE ENERGY-DELIVERY DEVICE AND SYSTEM, filed on Mar. 15, 2013 by Brannan et al., the entire contents of each of which are incorporated herein by reference, may be used in conjunction with the aspects and features of the present disclosure.

In addition to the EM tracking system, the surgical instruments, e.g., microwave ablation antenna assembly 160, may also be visualized by using ultrasound imaging work station 150. Ultrasound sensor 140, such as an ultrasound wand, may be used to image the patient's body during the microwave ablation procedure to visualize the location of microwave ablation antenna assembly 160 inside the patient's body. Ultrasound sensor 140 may have an EM tracking sensor embedded within or attached to the ultrasound wand, for example, a clip-on sensor or a sticker sensor. Ultrasound sensor 140 may be positioned in relation to microwave ablation antenna assembly 160 such that microwave ablation antenna assembly 160 is at an angle to the ultrasound image plane, thereby enabling the clinician to visualize the spatial relationship of microwave ablation antenna assembly 160 with the ultrasound image plane and with objects being imaged. Further, the EM tracking system may also track the location of ultrasound sensor 140. This spatial depiction of the ultrasound sensor 140 and the microwave ablation antenna assembly 160 is described in greater detail in U.S. Patent Application No. 62/154,924 entitled METHODS FOR MICROWAVE ABLATION PLANNING AND PROCEDURE, filed on Apr. 30, 2015 by Girotto, which is incorporated herein by reference. During surgery, one or more ultrasound sensors 140 may be placed on or inside the body of the patient. EM tracking system may then track the location of such ultrasound sensors 140 and microwave ablation antenna assembly 160 as they are moved relative to each other. It is also envisioned that ultrasound workstation 150 and its related components may be interchanged with real time fluoroscopy, MRI or CT imaging stations.

Figure 3:
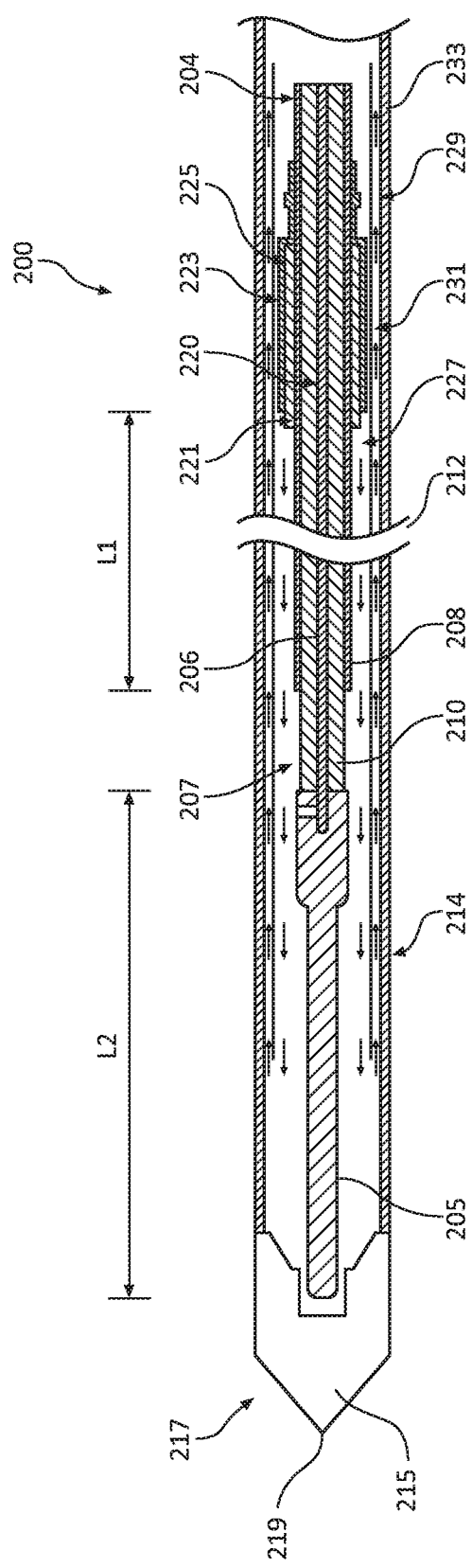
FIG. 3 is a cross-sectional view of a distal end of the antenna assembly of FIG. 3.

Referring now to FIG. 3, microwave ablation antenna assembly 160, microwave ablation generator 115, touch display computer 110, and peristaltic pump 117 are depicted schematically as housed on base unit 170 of system 10 (FIG. 1). Microwave ablation antenna assembly 160 is coupled to a microwave generator 115 via a flexible coaxial cable 116. Microwave generator 115 is configured to provide microwave energy at an operational frequency from about 915 MHz to about 2.45 GHz, although other suitable frequencies are also contemplated. Microwave ablation antenna assembly 160 may include a connection hub 162 for connection of coaxial cable 116, as well as the connection of a fluid inlet port 164 and a fluid outlet port 166. Fluid inlet port 164 permits the ingress of fluid into the microwave ablation antenna assembly 160 for cooling of components housed therein and control of the energy dissipation of microwave energy. Fluid outlet port 166 permits the egress of the fluid following circulation of the fluid through the microwave ablation antenna assembly 160.

The ports 164 and 166 are also coupled to a pump 117 that is, in turn, coupled to a supply tank 118 via a connection line 119a. Supply tank 118 may be a fluid filled bag (e.g., saline), as depicted in FIG. 3, or any other type of storage unit for any type of fluid. Pump 117 may be a positive displacement pump, such as a peristaltic pump. The supply tank 118 stores the fluid and may maintain the fluid at a predetermined temperature. The supply tank 118 may include a coolant unit (not explicitly shown) that cools returning liquid from the microwave ablation antenna assembly 160. In another embodiment, the fluid may be a gas and/or a mixture of liquid and gas. Pump 117 forces fluid from supply tank 118 through a supply line 119b into microwave ablation antenna assembly 160, such that heat is drawn away from the microwave ablation antenna assembly 160, which may enhance the overall ablation pattern, prevent damage to microwave ablation antenna assembly 160, and prevent harm to the clinician or patient. The fluid is returned to pump 117 and, ultimately, supply tank 118, via return line 119c and pump return line 119d. Connected to and branching from supply line 119b is an irrigation line 119e, which includes a valve 167 and an outlet nozzle 168. As will be described in more detail below (FIG. 7), during use, irrigation line 119e permits the egress of cooling fluid (e.g., saline) through outlet nozzle 168 into introducer 500 such that the space between the outer surface of microwave ablation antenna assembly 160 and introducer 500 is filled with cooling fluid. Additionally or alternatively, fluid may be ejected from the free end 503 of introducer 500 into a target site.

FIG. 3 illustrates the distal portion 200 of the microwave ablation antenna assembly 160. Distal portion 200 of microwave ablation antenna assembly includes a proximal radiating portion 212 having a length "L1," and a distal radiating portion 214 having a length "L2," including an electrically-conductive radiator 205 and a feed point 207 disposed between the proximal and distal radiating portions 212 and 214. A feedline 204 is formed of a coaxial cable having an inner conductor 206, and outer conductor 208, and a dielectric 210 separating the two. The feedline 204 is connected at its proximal end to flexible cable 116 (FIG. 3). The distal radiating portion 214 and the proximal radiating portion 212 may be either balanced (e.g., of equal lengths) or unbalanced (e.g., of unequal lengths). The proximal radiating portion 212 may be formed of a portion of the feedline 204, and particularly the outer conductor 208 extending between a balun 220 and the feedgap 216.

Referring still to FIG. 3, microwave ablation antenna assembly 160 also includes a balun (e.g., a choke) 220 disposed around the feedline 204. The balun 220 may be a quarter-wavelength balun formed of at least a dielectric layer 221 and a conductive layer 223. The conductive layer 223 may be shorted to the feedline 204 at the proximal end of the balun 220 by soldering or other suitable methods, or may be in electrical contact with a balun short 225 which itself is in electrical contact with the outer conductor 208 of the feedline 204. Microwave ablation antenna assembly 160 also includes a tip 215 having a tapered end 217 that terminates, in one embodiment, at a pointed end 219 to allow for insertion into tissue with minimal resistance. In cases where the microwave ablation assembly 160 is inserted into a pre-existing opening, tip 215 may be rounded or flat. The tip 215 may be formed from a variety of heat-resistant materials suitable for penetrating tissue, such as metals (e.g., stainless steel) and various thermoplastic materials, such as poletherimide, and polyamide thermoplastic resins.

The microwave ablation antenna assembly 160 includes fluid channels 227 and 229. Fluid channel 227 is spaced between the feedline 204 (including its electrically-connected components balun 220 and proximal and distal radiating portions 212 and 114) and an inner tube 231. Fluid channel 229 is formed between the inner tube 231 and an outer cannula 233 of the microwave ablation antenna assembly 160. Fluid channel 227 connects to fluid inlet port 164 and fluid channel 229 connects to fluid outlet port 166, thereby completing a fluid circuit from the fluid tank 118, through the pump 117 and through the microwave ablation antenna assembly 160.

Figure 4:
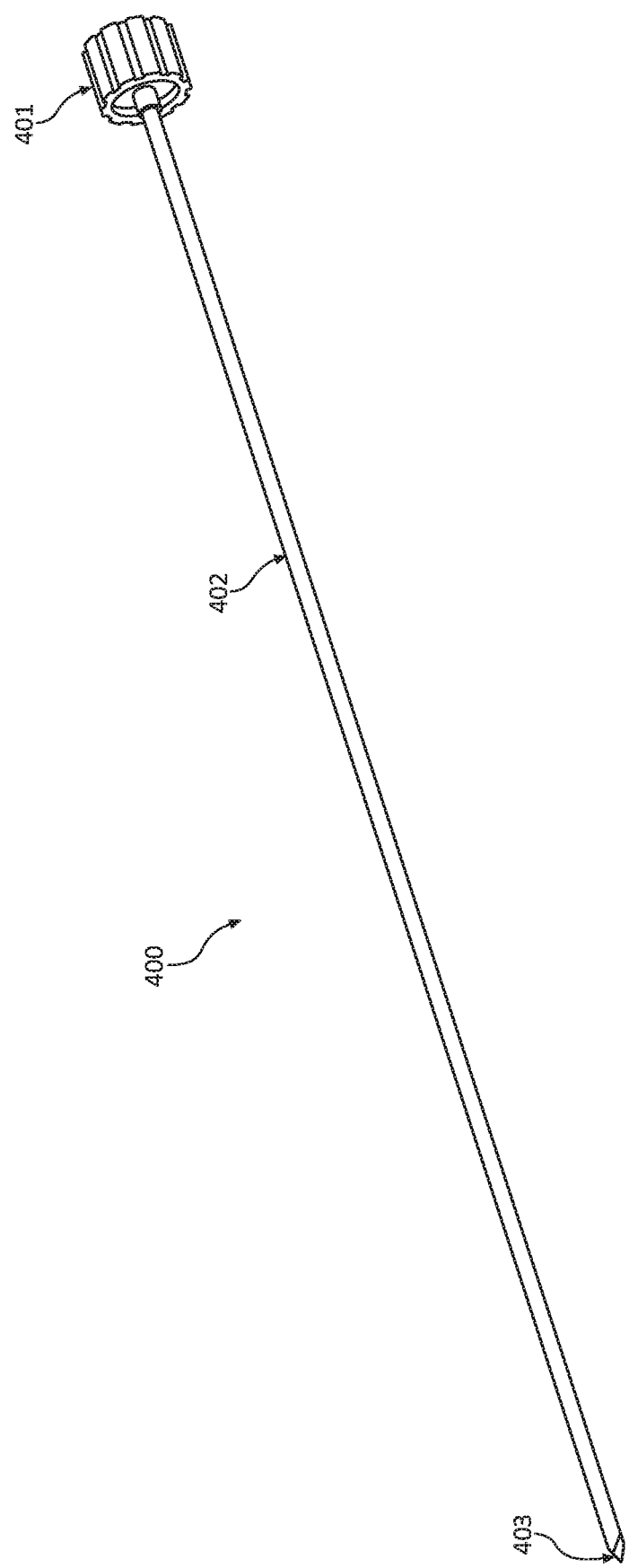
FIG. 4 is a side view of a stylus.
Figure 5:
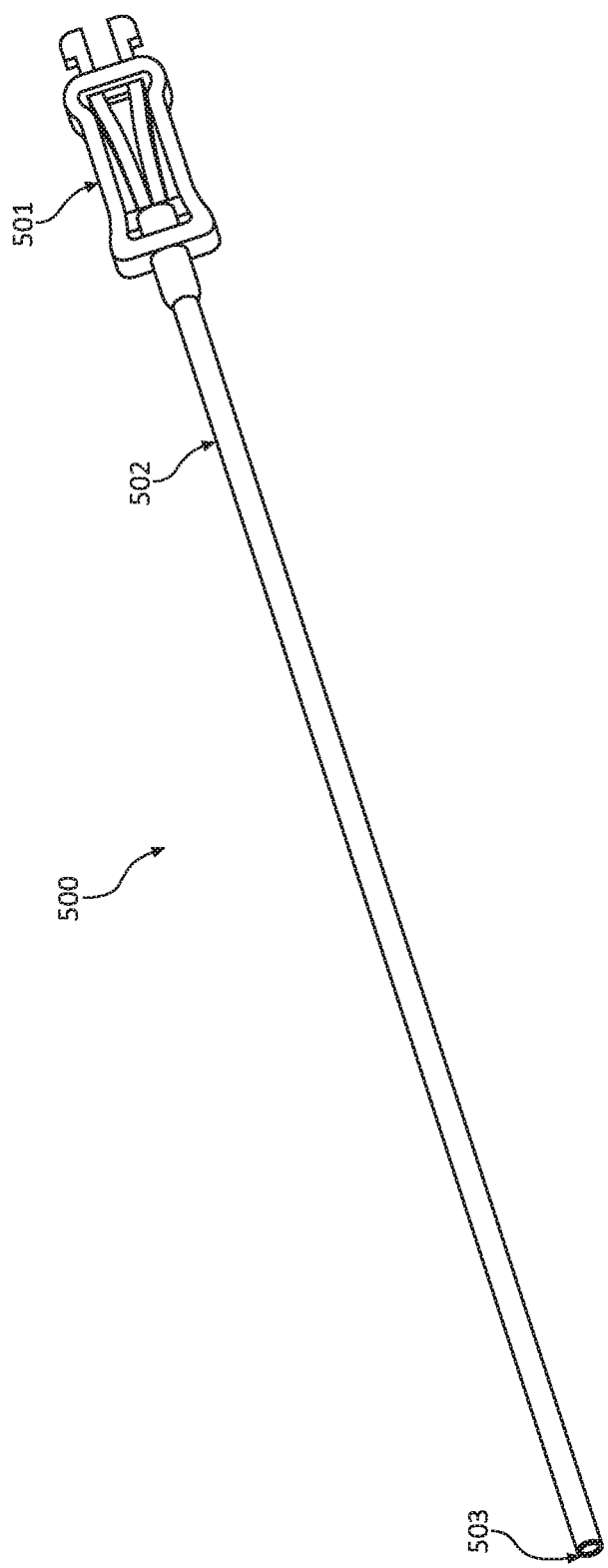
FIG. 5 is a side view of an introducer.

Referring now to FIG. 4, an example of a stylus 400 is generally depicted, including a cap 401, a shaft 402, and a tip 403. With reference to FIG. 5, an introducer 500 is generally depicted and includes a fitting 501, a shaft 502, and a free end 503. Stylus 400 (FIG. 4) is fabricated such that it may be disposed within introducer 500 (FIG. 5) in coaxial arrangement. In use, stylus 400 and introducer 500 are inserted into a patient's body together (FIG. 6, access assembly 600), with the tip 403 of stylus 400 projecting slightly beyond the free end 503 of introducer 500 for piercing the skin. After stylus 400 and introducer 500 have reached their target destination (e.g., the tumor site), stylus 400 is removed. Microwave ablation antenna assembly 160 is then inserted and advanced down shaft 502 of introducer 500 (FIG. 7, as treatment assembly 700) such that treatment of the target site can be initiated.

Referring back to FIG. 4, stylus 400 may be formed of a metallic or non-metallic (e.g., ceramic MRI compatible) rigid or semi-rigid material having the ability to traverse tissue. Preferably, stylus 400 is formed of a material that is visible in real time ultrasound, CT, MRI, or other imaging systems. Cap 401 of stylus 400 may have a lumen (not shown) for ejectment of fluids (e.g., blood), or so that other devices (e.g., guide wires) may be inserted into the lumen through shaft 402 of stylus 400. Cap 401 may also have a lock fitting for attachment to other devices, such as fitting 501 of introducer 500, microwave ablation antenna assembly 160, guide wires, extending working channels, or the like. Shaft 402 of stylus 400 may be any length (e.g., 10 cm, 15 cm, 20 cm, etc.) and may have a substantially straight or, alternatively, a curved profile. Stylus 400 may also be articulable and/or steerable to accommodate a specific surgical procedure, a specific luminal structure, specific target tissue, a clinician's preference, etc. For example, a user may manipulate shaft 402 of stylus 400 to adopt a curved profile such that stylus 400 may traverse critical tissue structures or narrow pathways to reach a target site. Tip 403 of stylus 400 may be a sharp edge for penetrating skin, such as a single bevel, dual bevel, or the like.

Figure 6:
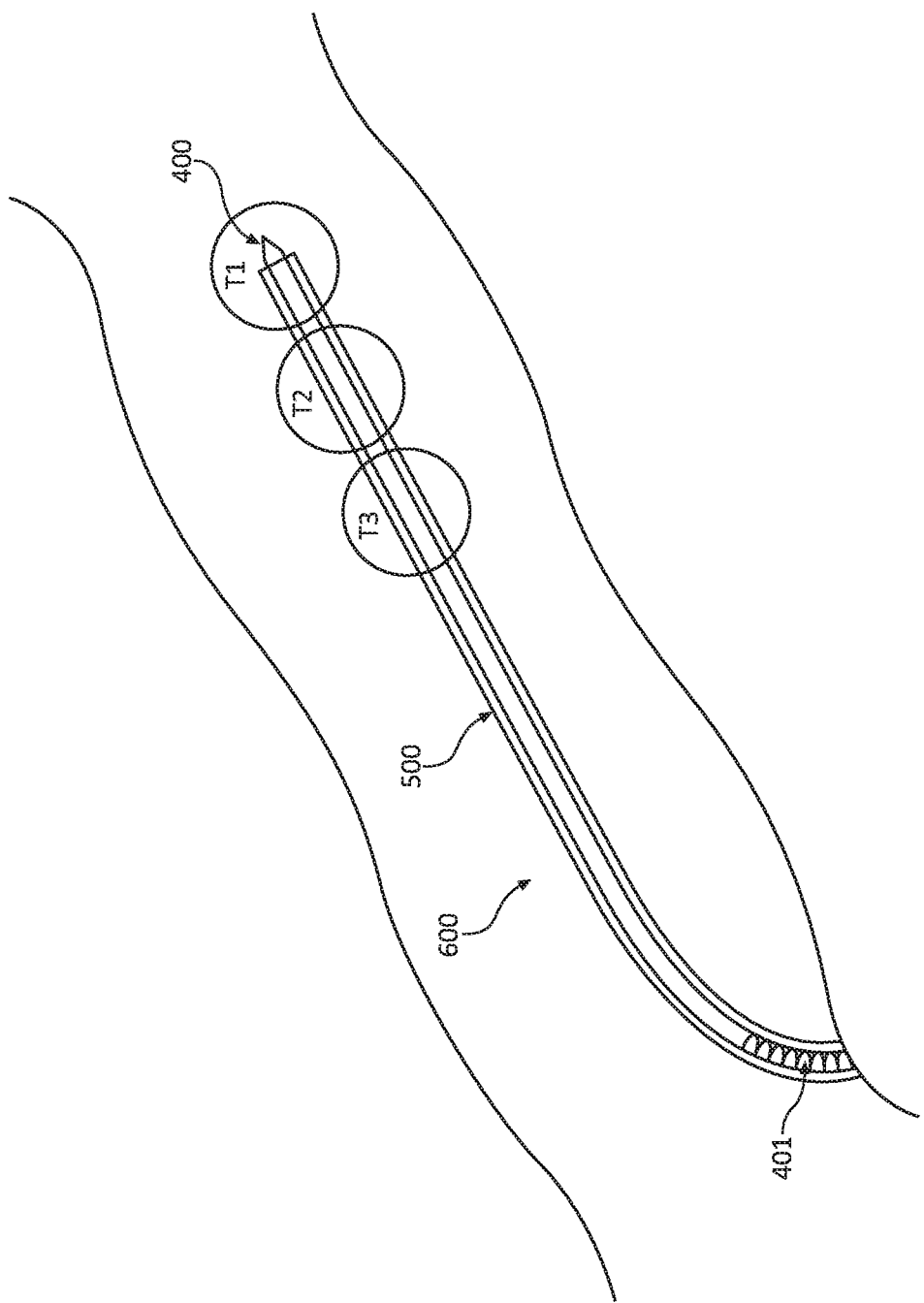
FIG. 6 is a schematic diagram of a cross-sectional view of an access assembly placed into tissue.

With reference to FIG. 5, introducer 500 may be formed from Polyether ether ketone (PEEK), fiberglass, or any other plastic, polymer, or the like. Preferably, introducer 500 is formed of a material visible in real time ultrasound, CT, or MRI imaging. Depth markers may be placed on shaft 502 of stylus 500 for indicating distance (e.g., in real time ultrasound, CT, or MRI imaging). Introducer 500 may be rigid, semi-rigid, or flexible and may be formed of a shape-memory material, such that it can adopt and maintain the profile (e.g., curved) of steerable stylus 400 (FIG. 6, described in more detail below). Fitting 501 of introducer 500 may have a lumen (not shown) for connection and/or insertion of other devices (e.g., guide wires, extended working channels, microwave ablation antenna assembly 160, stylus 400, etc.). Shaft 502 of introducer 500 may be fabricated of any length suitable to reach a target site. Likewise, shaft 502 of introducer 500 may have any suitable outer diameter for passage into and through tissues, vessels, or other luminal networks, or any suitable inner diameter (e.g., a lumen) for the insertion of other devices 502 (e.g., microwave ablation antenna assembly 160, stylus 400, etc.) through the inside of shaft 503.

Referring now to FIG. 6, an access assembly 600 is depicted, which includes stylus 400 and introducer 500, as shown inside a body cavity. During use, stylus 400 and introducer 500 are inserted together as access assembly 600, with stylus 400 inserted into introducer 500 and aligned coaxially therewith. Tip 403 of stylus 400 protrudes from free end 503 of introducer 500 for puncturing skin and advancing access assembly 600 to a desired target site. Stylus 400 is manipulated, articulated, and/or steered to avoid critical tissue structures and to reach the desired target site. For example, as shown in FIG. 6, stylus 400 may include an articulation joint 410, which may be articulated by using a dial or other attachment (not shown) that is separate from or integral to cap 401. Advantageously, access assembly 600 assists in eliminating stresses applied to microwave ablation antenna assembly 160 during insertion because all of the tissue separation is done by access assembly 600 and not microwave ablation antenna assembly 160.

With continued reference to FIG. 6, introducer 500 dynamically adopts and maintains the path of stylus 400 even after formed stylus 400 is removed. Although stylus 400 and introducer 500 are shown as having a single curved configuration, it should be appreciated that stylus 400 and introducer 500 of access assembly 600 may adopt a trajectory having any configuration (e.g., straight, a plurality of curves, etc.) for reaching challenging targets. After the desired target site has been reached, stylus 400 may be withdrawn from introducer 500, with introducer 500 maintaining the trajectory that formed stylus 400 had prior to its removal from introducer 500. After removal of stylus 400, introducer 500 may be kept in place by the body's natural pressures. In other words, removal of the stylus 400 leaves behind the flexible introducer 500, which can be compressed and held in place by the tissue in which it is inserted. As such, introducer 500 maintains access to the target site and is ready for insertion of microwave ablation antenna assembly 160 for treatment of the target site.

If multiple tumors are identified at several remote locations within the same patient, the same procedure described above can be repeated. For example, multiple introducers 500 may be placed and left at several target sites within the body. After a surgeon finishes ablating one target site and removes microwave ablation antenna assembly 160 from a first introducer 500, the surgeon may move on to the second introducer 500, insert microwave ablation antenna assembly 160, and begin ablation at a second target site, and so on and so forth. Thus, advantageously, a surgeon may reuse a single microwave ablation antenna assembly 160 to sequentially ablate all required target sites. The aforementioned procedure reduces the cost of procedures which require the placement of multiple antennas. Further, introducer 500 and stylus 400 are less likely to move after placement as compared to microwave ablation antenna assemblies which require separate cooling fluid lines, energy feed lines, and the like, all of which exert force on the microwave ablation antenna assembly and can cause it to move after placement. Having none of these encumbrances, introducer 500 and stylus 400 are less prone to movement after placement in a target site.

Figure 7:
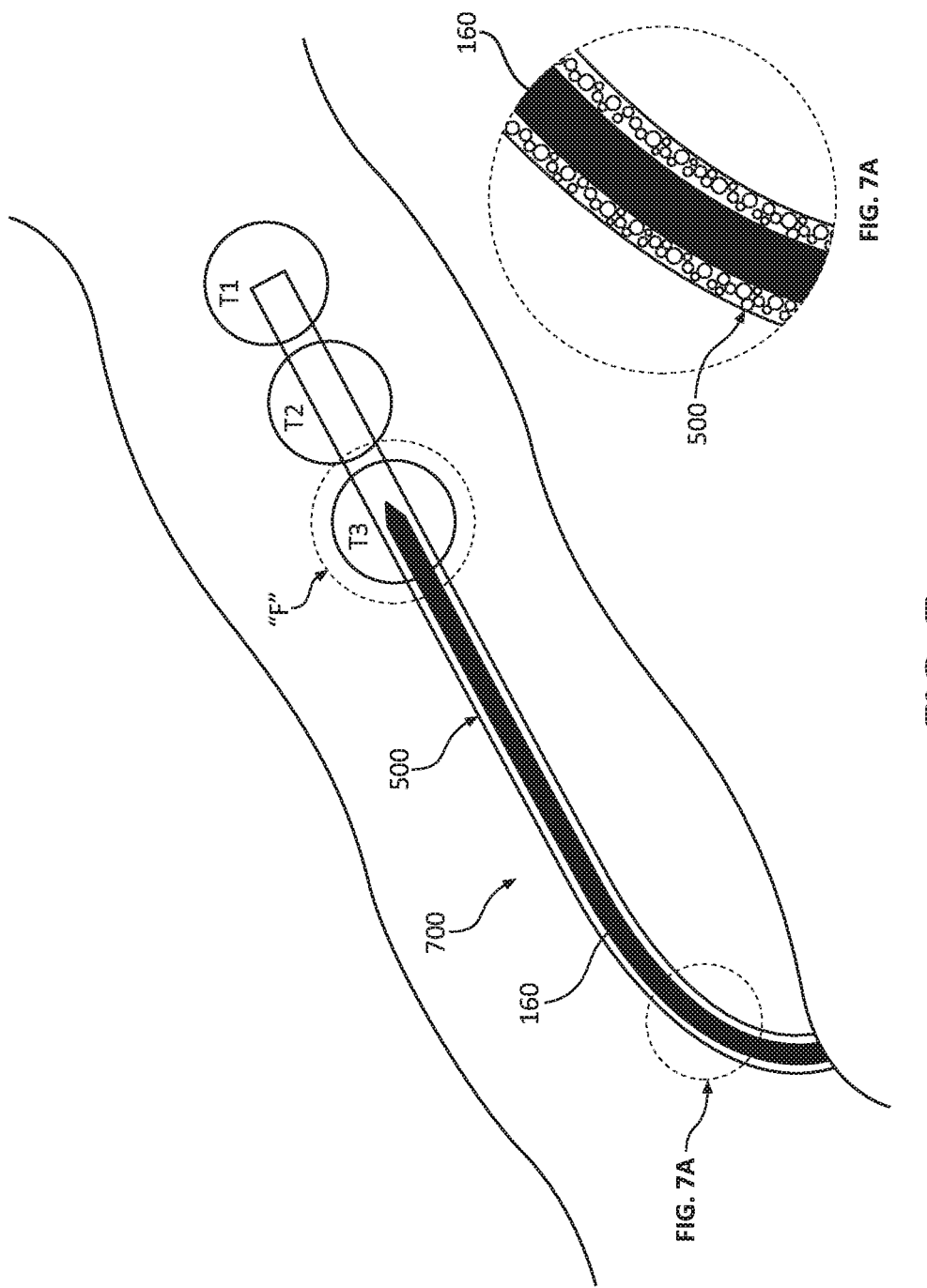
FIG. 7 is a schematic diagram of a cross-sectional view of a treatment assembly placed into tissue.

Referring now to FIG. 7, a treatment assembly 700 is shown, including microwave ablation antenna assembly 160 and introducer 500. After the removal of stylus 400 from introducer 500, microwave ablation antenna assembly 160 is inserted into introducer 500 and aligned coaxially therewith. Advantageously, introducer 500 is formed from a non-conductive (e.g., non-metallic) material allowing microwave ablation antenna assembly 160 to radiate through introducer 500. Specifically, proximal radiating portion 212 and distal radiating portion 214 of distal portion 200 of microwave ablation antenna assembly 160 can radiate energy and generate an ablation field "F" (FIG. 7) through any portion of introducer 500, which allows treatment of target sites (e.g., "T1," "T2," and "T3") beyond just the free end 503 of introducer 500, as shown in FIG. 7. As such, microwave ablation antenna assembly 160 can be retracted or advanced through introducer 500, so that target sites anywhere along the trajectory of introducer 500 can receive the optimal amount of radiation from the radiating portions 212, 214 of microwave antenna assembly 160. As shown in FIG. 7, after target sites T1 and T2 have been treated, microwave ablation antenna assembly 160 may be retracted within introducer 500 until it is proximal to target T3. After microwave ablation antenna assembly 160 is in place, an ablation field "F" is generated for treatment of target T3.

Figure 2:
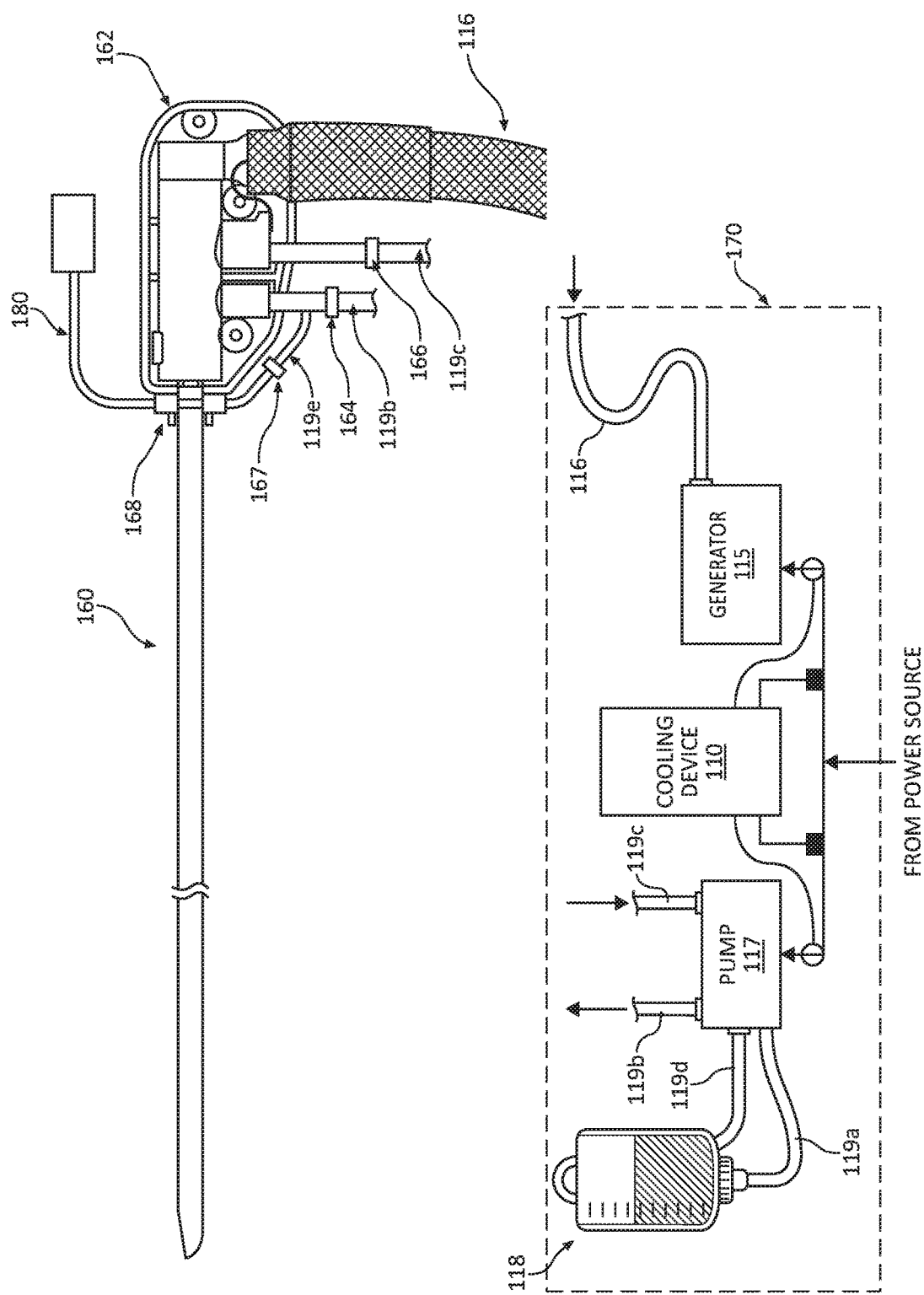
FIG. 2 is a side, partial cross-sectional view of a fluid cooled microwave ablation antenna assembly and base unit of the system of FIG. 1.

Moreover, radiating through introducer 500 helps prevent the charring of tissue and/or the sticking of microwave ablation antenna assembly 160 to tissue during ablation. Thus, by preventing charring and sticking, wavelength elongation and/or reduction of the dielectric constant is also prevented. In order to further enhance the overall ablation field, fluid is allowed to flow between the outer surface of microwave ablation antenna assembly 160 and introducer 500 via irrigation line 119e and outlet nozzle 168 of microwave ablation antenna assembly 160 (FIG. 2). The cooling fluid (e.g. saline) has an unchanging dielectric constant versus air or other fluids. As such, cooling and/or surrounding the external surface of microwave ablation antenna assembly 160 with fluid maintains the dielectric constant, reduces or eliminates wavelength elongation, enables larger and more uniform ablation zones, and enhances impedance matching over internal cooling of microwave ablation antenna assembly 160 alone.

Free end 503 of introducer 500 may have an airtight or watertight seal (e.g., a gasket and/or through an interference fit with microwave ablation antenna assembly 160) to prevent the ejectment of fluid into a target site. Alternatively, free end 503 of introducer 500 may allow for the passage of fluid into a target site. The expulsion of fluid from the free end 503 of introducer 500 may be used to hydro-defect or move tissue structures out of the path of treatment assembly 700, or to positively affect the dielectric constant of the area proximate to the target site. Referring back to FIG. 1, a supply line 180 may be connected to a source of therapeutic (e.g., chemotherapeutic) agents, which may then be delivered into and/or out of introducer 500. The therapeutic agents may be, for example, thermo-sensitive or activated upon the radiation from microwave ablation antenna assembly 160.

Figure 8:
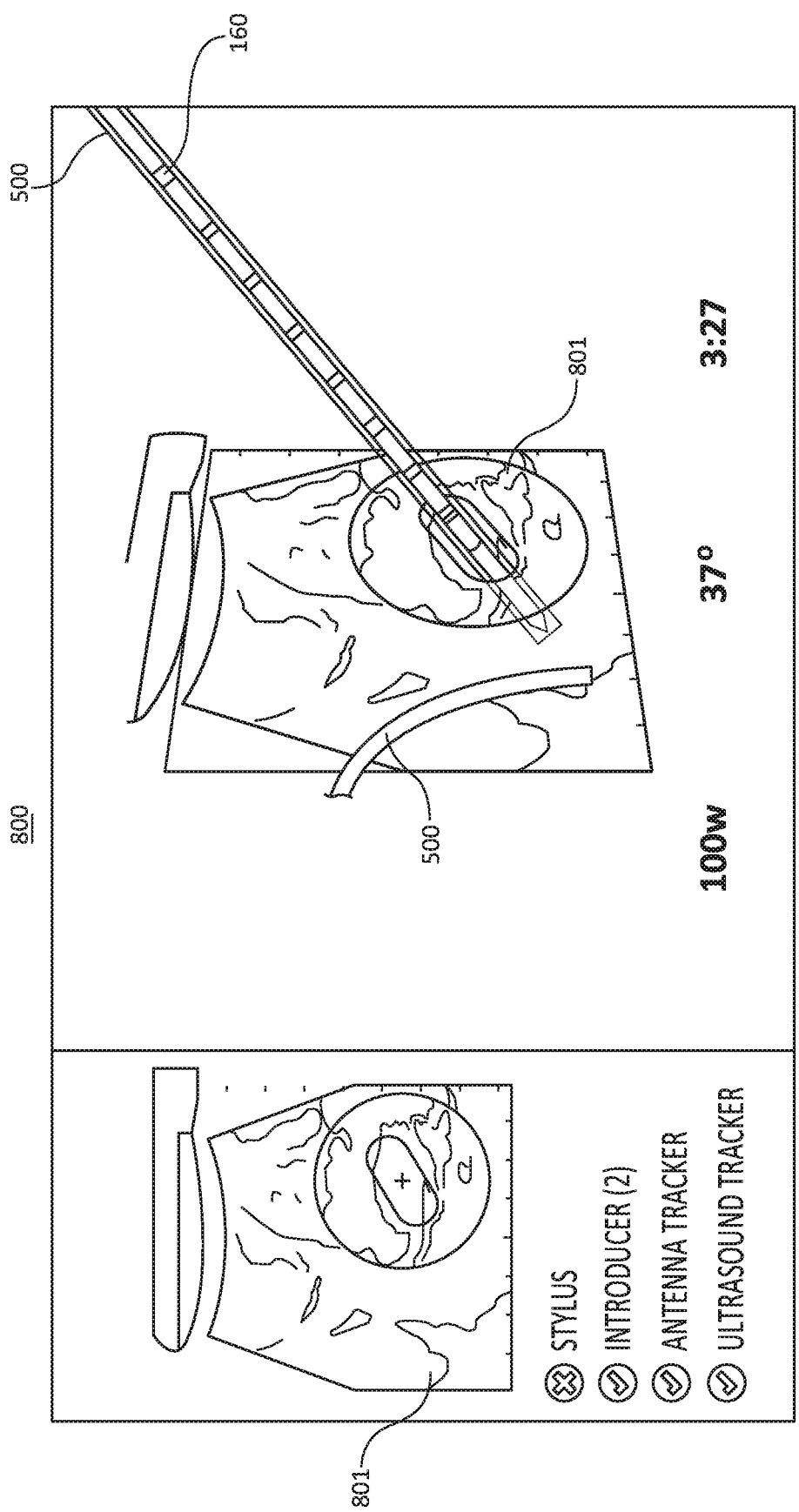
FIG. 8 is an illustration of a user interface presenting a view during a microwave ablation treatment.

Referring now to FIG. 8, an example screen 800 is shown, which may be displayed on touch display computer 110 or display 130 during a microwave ablation procedure. Screen 800 includes a view 801 of the live 2D ultrasound (or real time CT, MRI, fluoroscopy) images captured during the procedure. Screen 800 may aid a user in the positioning and/or the resulting location of access assembly(s) 600, treatment assembly(s) 700, stylus(s) 400, introducer(s) 500, microwave ablation antenna assembly(s) 160, or any other devices used in the procedure. Ultrasound sensor 140 may be positioned in relation to the aforementioned devices such that they are at an angle to the ultrasound image plane, thereby enabling the clinician to visualize their spatial relationship with the ultrasound image plane and with objects being imaged. As can be appreciated, other imaging techniques such as fluoroscopy, CT and MRI may be used with and/or separately from ultrasound workstation 150 to e.g., visualize and confirm placement of stylus 400, introducer 500, and microwave ablation antenna assembly 160 into a target.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation system comprising:
   an introducer having a lumen therethrough and a seal disposed at a distal end of the introducer;
   a stylus configured for slidable engagement within the lumen of the introducer;
   a microwave ablation antenna configured to deliver energy to a target in a target site during an ablation procedure, wherein the microwave ablation antenna is configured for slidable engagement within the lumen of the introducer after the stylus is removed from the lumen of the introducer, a distal end of the microwave ablation antenna including a portion configured to interface with the seal disposed at the distal end of the introducer to prevent ejection of fluid from within the lumen of the introducer into the target site when the microwave ablation antenna is interfaced with the seal and extended distally beyond the distal end of the introducer; and
   an electromagnetic navigation system configured to track a position, and facilitate navigation, of at least one of the introducer, the stylus, or the microwave ablation antenna to the target.

2. The microwave ablation system of claim 1, wherein the introducer is formed from a non-conductive material that allows the microwave ablation antenna to radiate microwave energy throughout an entire length of the introducer.

3. The microwave ablation system of claim 1, wherein the introducer is formed from a material selected from the group consisting of Polyether ether ketone and fiberglass.

4. The microwave ablation system of claim 1, wherein the introducer has a first end, a second end, and a shaft disposed therebetween, wherein:
   the first end has a first aperture and a fitting configured for engagement with the microwave ablation antenna and the stylus; and
   the second end has a second aperture.

5. The microwave ablation system of claim 1, wherein the stylus is configured to articulate and adopt at least one curved configuration to navigate to the target.

6. The microwave ablation system of claim 5, wherein the introducer is formed from a shape-memory material and configured to adopt and maintain the at least one curved configuration of the stylus.

7. The microwave ablation system of claim 6, wherein the introducer maintains the at least one curved configuration defined by the stylus after the stylus has been removed from the introducer.

8. The microwave ablation system of claim 1, further comprising a fluid configured to be introduced into the lumen of the introducer.

9. The microwave ablation system of claim 8, wherein the fluid is disposed between an outer surface of the microwave ablation antenna and the lumen of the introducer.

10. The microwave ablation system of claim 1, further comprising a therapeutic agent configured to be introduced into the lumen of the introducer.

11. The microwave ablation system of claim 10, wherein the therapeutic agent is thermo-sensitive and configured to react with the energy radiated from the microwave ablation antenna.

12. The microwave ablation system of claim 1, wherein the electromagnetic navigation system is used in conjunction with real time ultrasound, fluoroscopy, CT, or MRI imaging.

* * * * *